United States Patent
Städler et al.

(10) Patent No.: US 12,116,223 B2
(45) Date of Patent: Oct. 15, 2024

(54) STACKING DEVICE FOR MICROTITER PLATES

(71) Applicant: INTEGRA Biosciences AG, Zizers (CH)

(72) Inventors: Andreas Städler, Felsberg (CH); Hans-Jürgen Tiedtke, Hombrecktikon (CH)

(73) Assignee: Integra Biosciences AG, Zizers (CH)

( * ) Notice: Subject to any disclaimer, the term of this patent is extended or adjusted under 35 U.S.C. 154(b) by 191 days.

(21) Appl. No.: 17/847,403

(22) Filed: Jun. 23, 2022

(65) Prior Publication Data
US 2022/0411210 A1 Dec. 29, 2022

(30) Foreign Application Priority Data

Jun. 24, 2021 (CH) .................................... 00737/21

(51) Int. Cl.
*B65G 59/06* (2006.01)
*G01N 35/02* (2006.01)
*G01N 35/04* (2006.01)

(52) U.S. Cl.
CPC .......... *B65G 59/063* (2013.01); *G01N 35/028* (2013.01); *G01N 2035/042* (2013.01); *G01N 2035/0425* (2013.01)

(58) Field of Classification Search
CPC .......... G01N 2035/0425; B65G 59/063; B65G 59/062; B65G 59/066; B65G 47/1407; B65G 47/295; B65G 59/105; C12M 23/48; A47F 1/08; A47F 1/04; B65D 83/0409; B65D 2583/0481; B65D 83/0418
See application file for complete search history.

(56) References Cited

U.S. PATENT DOCUMENTS

| 3,658,194 A * | 4/1972 | Gendron .............. B65G 59/107 414/795.8 |
| 4,094,236 A * | 6/1978 | Holmes .................. A23G 9/286 426/123 |

(Continued)

FOREIGN PATENT DOCUMENTS

WO 2006017737 A2 2/2006

OTHER PUBLICATIONS

CH 00737/21 Search Report dated Nov. 8, 2021, 4 pages.

*Primary Examiner* — Gregory W Adams
(74) *Attorney, Agent, or Firm* — Andrus Intellectual Property Law, LLP

(57) ABSTRACT

A device for receiving, stacking, and removing microplates is presented and described. The device comprises a tower for stacking the microplates, wherein a microplate comprises a container and, optionally, a lid. There is a retaining device at the lower end of the tower, which has a first retaining tool and a second retaining tool, and preferably partially encompasses a microplate. The first retaining tool is designed to hold a microplate in a form-fitting manner. The second retaining tool is designed to fix a container in the microplate in place in a frictional manner. The first retaining tool is above the second retaining tool in the stacking direction. A system that comprises the device described above, a dispenser device, and a transport device, is also disclosed. The dispenser device is used to fill microplates, and the transport device is used to add and remove microplates to and from the device.

14 Claims, 6 Drawing Sheets

(56) References Cited

U.S. PATENT DOCUMENTS

| | | | | |
|---|---|---|---|---|
| 4,170,861 A * | 10/1979 | Snyder | ................... | C12M 29/00 |
| | | | | 53/381.4 |
| 4,477,219 A * | 10/1984 | Sauder | ................. | B65G 59/062 |
| | | | | 156/565 |
| 4,529,101 A * | 7/1985 | Orlowski | ............. | B65G 59/101 |
| | | | | 221/11 |
| 4,971,514 A | 11/1990 | Hunter | | |
| 5,176,494 A * | 1/1993 | Nigrelli | ................ | B65G 59/066 |
| | | | | 414/797.6 |
| 5,348,441 A * | 9/1994 | Takemasa | ............. | B23P 19/001 |
| | | | | 414/795.8 |
| 5,906,472 A * | 5/1999 | Nakamura | ......... | H05K 13/0061 |
| | | | | 221/222 |
| 6,193,102 B1 | 2/2001 | Bevirt et al. | | |
| 6,558,110 B2 * | 5/2003 | Lu | ..................... | H01L 21/68707 |
| | | | | 221/297 |
| 9,045,723 B2 * | 6/2015 | Brelivet | ................ | C12M 33/04 |
| 9,389,050 B1 * | 7/2016 | Chen | ........................... | F41J 9/30 |
| 2001/0048899 A1 | 12/2001 | Marouiss et al. | | |
| 2008/0028835 A1 * | 2/2008 | Higuchi | ................ | G01N 35/04 |
| | | | | 73/53.01 |

* cited by examiner

STACKING DEVICE FOR MICROTITER PLATES

CROSS REFERENCE TO RELATED APPLICATIONS

The present application claims priority to Swiss Patent Application No. 00737/21 filed Jun. 24, 2021.

TECHNICAL FIELD OF THE INVENTION

The invention relates to a device for receiving, stacking and removing microplates, also known as microtiter plates, and a system and a method for adding or removing microplates to or from a stack.

BACKGROUND OF THE INVENTION

A large number of microplates are used in laboratories for various purposes. For this reason, a quick processing thereof is of major importance with regard to the overall efficiency of a procedure. The microplates used in a laboratory normally comprise a container and in some cases, a lid.

Microplates are processed quickly in that, among other things, the microplates are stacked. The stacked microplates are then removed individually, and processed in accordance with the use for which they are intended. The microplate lid must be removed from its container for this. The removal of the microplate lid after taking it from the stack is a technological challenge with regard to the design of an efficient procedure while maintaining the necessary precision. The separation of the lid on the lowest microplate from the container in the microplate above it also requires an additional effort.

One such device for stacking and removing microplates is disclosed in US Pat. 2015/0110690 A1. The device comprises a housing for receiving and stacking microplates. There are retaining elements at the lower end of the housing, which can each hold one lid for a microplate. In the starting position, the retaining elements hold the lid for the lowest microplate. A transport device has direct access to the lowest microplate in the stack, and can raise or lower the stack through its own up and down movement, although the lowering movement of the microplates may be restricted by the retaining element. The retaining element is released in order to take the lowest microplate away. This results in the entire weight of the stack resting on the lifting device. The lifting device then moves down until the retaining element can obtain a form-fitting connection with the lid on second-lowest microplate. At this point, the previously lowest microplate rests with the container from the originally second-lowest microplate on the lifting device. The container from the originally second-lowest microplate must be removed from the lifting device after the lifting device has left the device for stacking the microplates with the microplate placed thereon. There is a gripping device for this, which forms a separate component located on the side of the device for stacking the microplates. This means that a separate device in the form of a gripping device must participate in the process, resulting in a larger device on the whole, and the microplates having to travel a greater distance. Furthermore, it has been shown in practice that when generating or releasing a form-fitting connection between a retaining element and a microplate, the microplate may be subjected to small, jolting movements. This is undesirable if the microplate has been filled, and should ideally be avoided.

OBJECT OF THE INVENTION

It is therefore the object of the present invention to create a device for stacking microplates that is compact and functions reliably. The proposed device should function reliably under a variety of basic conditions.

SUMMARY OF THE INVENTION

The above object is achieved with a device for receiving, stacking and removing microplates that has the features described herein.

The invention relates to a device for receiving, stacking, and removing microplates. The device comprises a tower for stacking microplates, and a retaining device at the lower end of the tower, which contains a first and second retaining tool, and preferably partially encompasses a microplate. A microplate comprises a container and, optionally, a lid. The first retaining tool is designed to fix a container in the microplate in place in a frictional manner. The first retaining tool is located above the second retaining tool in the stacking direction.

The device according to the invention has a retaining device at its lower end. The retaining device comprises two vertically arranged retaining tools, wherein the upper retaining tool can hold a microplate in a form-fitting manner, and the lower retaining tool can hold it in a frictional manner. The form-fitting connection obtained with the first retaining tool is such that it prevents downward movement of the microplate, and can therefore support the weight of all of the microplates in the device. This weight may vary significantly, depending on the number of microplates. One advantage of the form-fitting connection is that it does not need to be adjusted for different weights. The form-fitting connection must only be robust enough to support the maximum weight it may be subjected to. A lower weight has no effect on the form-fitting connection. When the first retaining tool fixes a microplate in place, all of the other microplates above it rest thereon, thus contributing to the overall weight acting on the first retaining tool. This weight primarily depends on the number of microplates above it, and the extent to which they are filled, and may fluctuate significantly, as noted above.

Because the first retaining tool supports the weight of all of the microplates resting on it, the second retaining tool must only fix one microplate in place, and does not need to support the weight of other microplates. For this reason, the frictional connection of the second retaining tool can be set in accordance with this condition, such that the size of the second retaining tool can be adapted thereto. One advantage of the frictional connection, which is generated by the second retaining tool on the microplate, is seen in the removal and addition of microplates. The transport device for removing and adding microplates can receive or deliver the lowest microplate without moving the microplate when transferring it from the device according to the invention to the transport device, or vice versa.

Advantageously, the first retaining tool has a gripper, and this gripper is designed to hold the microplates in a form-fitting manner. This gripper is elongated in the direction of its movement. It is attached at one end, and the other end is designed to grip or retain an object. The gripper is able to support a vertical weight, acting at a right angle to its horizontal extension. The gripper on the first retaining tool supports the weight of the microplates resting on it in the device according to the invention. Because of its elongated shape, the gripper fulfills this task with a minimal amount of material, and occupies a minimal amount of space. The gripper preferably extends almost to the lateral walls of the microplate container in a tower when fully extended. The gripper must come close enough to the lateral wall of the microplate to be able to reach under the edge of the lid and form a form-fitting connection therewith. The extension of the gripper must not be so great that it comes in contact with the lateral wall of the microplate container in doing so.

There are preferably two grippers on the first retaining tool. The use of two grippers reduces the weight that each has to support by half, and also results in a greater stability when holding a microplate. When the balance point of the microplate is basically halfway between the two grippers, the microplate will not tip unless excessive force is applied thereto. The retaining device ideally encompasses the lowest microplate in a stack such that microplate resting on the grippers in the first retaining tool is unable to rotate, and is in a stable position.

A bolt is attached to the second retaining tool in a preferred embodiment, and the bolt holds the microplate container in place. The microplate can comprise a container and a lid, among other things. The second retaining tool preferably fixes the microplate container in place. This bolt is a cylindrical element, the length of which is greater than its diameter. The bolt can be placed such that its circular end surface can come in contact with the microplate. The bolt must be moved longitudinally for this.

There are preferably two bolts on the second retaining tool. The use of two bolts on the second retaining tool means that the force applied by each bolt to the microplate is halved. Because the force is only applied by the bolt to the microplate at the circular end surface thereof, the pressure exerted by the bolt on the microplate is proportional to this force, and can therefore also be comparatively high. By distributing this force between two bolts, the pressure exerted on the microplate is reduced, as is the load to the microplate.

In another preferred embodiment, the first retaining tool is supported by a first spring element on the retaining device, wherein this first spring element is preferably a compression spring. The first retaining tool is therefore under tension in its starting position, and can move in the direction of the compression spring when actuated.

The second retention tool is advantageously supported on the retaining device with a second spring element, wherein this second spring element also comprises a compression spring. As specified above, the second retaining tool is also under tension in its starting position, and also moves in the direction of the compression spring when actuated.

In another preferred embodiment, the first and second retaining tools are placed on the retaining device such that they can move toward the middle of the tower. The microplates are stacked in the middle of the tower. In this manner, the movement of the two retaining tools toward the middle of the tower forms the most direct and simplest possibility for obtaining contact between the two retaining tools and a microplate. Because the two retaining tools only have to move in a linear direction, they can have a structurally simple design. Furthermore, the unidirectional linear motion increases the reliability of the movement of the retaining tool.

A slide bar is preferably attached to the retaining device, which triggers the movement of the two retaining tools. The movement of the slide bar can therefore trigger the movement of both the first and second retaining tools. This means that only one element needs to be operated in order to trigger the movement of the two retaining tools. This also results in a more compact structure for the retaining tools, because they do not each need a separate triggering element for initiating movement.

The slide bar is preferably placed on the retaining device and connected to the retaining tools such that the slide bar triggers the movement of the first retaining tool in a first step, and the movement of the second retaining tool in a second step. When the retaining tools are at rest, the first retaining tool is moved with a first movement of the slide bar. The slide bar can then be returned to its original position after the first step, at which point the first retaining tool returns to its starting position, without the second retaining tool being moved. The movement of the second retaining tool is triggered by the movement of the slide bar in a second step. This means that the movement of the second retaining tool requires that the first retaining tool is in its extended position. Starting from when the two retaining tools are in the starting position, a form-fitting connection is first obtained with the first retaining tool. A frictional connection is then obtained with the second retaining tool, which is then released first when the slide bar is moved back toward its starting position. As the slide bar continues to move back to its starting position, the form-fitting connection of the first retaining tool is then released as the final step.

The retaining tool in another preferred embodiment has two first and second retaining tools, each of which lie opposite one another. With opposing retaining tools, the microplates can be fixed in place from two sides simultaneously. This results in a reliable fixing of the microplates in place. Ideally, the opposing retaining tools are moved simultaneously. This also results in a greater number of points at which force is exerted by the retaining tools on the microplates, thus reducing the load to the microplates at each point.

An intermediate plate can be placed between each of the stacked microplates. The intermediate plate increased the vertical distance between each microplate level for inserting the gripper on the retaining device. This reduces the precision requirements for controlling the movement of the gripper, resulting in a more reliable functioning of the gripper such that it can have a simpler construction. After inserting the gripper into an intermediate plate, it then bears the weight of the intermediate plate and all of the microplates above it.

A second aspect of the invention relates to a system that comprises a device according to the invention for receiving, stacking, and removing microplates, a dispenser device for filling microplates, and a transport device for adding and removing microplates to and from the device. The transport device transports the microplates between the dispenser device and the stacking device. The three devices in the system can form an integral unit or they can be structurally separate. It is also conceivable that just two of the three devices are structurally connected to one another. Ideally, the transport device moves the microplates toward the stacking device. This allows for both an insertion of the microplates into the device according to the invention from below, as well as removal thereof from the device according to the invention.

The system comprises a first and second device for receiving, stacking, and removing microplates in a preferred embodiment, which both share a single transport device. The two devices for receiving, stacking, and removing microplates share one transport device. Ideally, the first device contains empty microplates, which are then transferred to the second device after they are filled. The transport from the first device to a dispenser device and then to the second device takes place with the same transport device.

Another aspect of the invention relates to a method for adding microplates to a stack of microplates, or removing microplates from a stack of microplates, in which the stack is vertical. In this method, a microplate is added to a stack from below, or the lowest microplate is removed from the stack, and the lowest and second-lowest microplates are each held by retaining tools that can move in a plane, and are arranged vertically, while a transport device that can move in at least two directions adds a new microplate to the stack from below, or removes the lowest microplate from the stack. The microplates are stacked vertically. The upper retaining tool holds the respective microplate with a form-fitting connection thereto, and the lower retaining tool holds the respective microplate with a frictional connection thereto.

Because of the movement of the transport device in one direction, a microplate can be removed from the stack of microplates or added thereto with the proposed method. This reduces the distance that the transport device must travel with a microplate. A quicker processing of the microplates is obtained in this manner, and there is a lower chance of external effects acting on the microplates.

The method preferably comprises the following steps when removing a microplate from the stack:
 a) the transport device is placed under the lowest microplate,
 b) the frictional connection between the lowest microplate and the lower retaining tool is released such that the lowest microplate rests on the transport device,
 c) the transport device is moved upward until the lowest microplate resting on the transport device comes in contact with the second-lowest microplate,
 d) the form-fitting connection between the second-lowest microplate and the upper retaining tool is released such that the stack of microplates rests on the transport device,
 e) the transport device is moved downward until the third-lowest microplate is at the height of the upper retaining tool,
 f) the third-lowest microplate is held in a form-fitting manner by the upper retaining tool,
 g) the transport device is moved downward until the second-lowest microplate is at the height of the lower retaining tool,
 h) the second-lowest microplate can then be held by the lower retaining tool in a frictional manner, and
 i) the transport device takes the lowest microplate away.

When adding a microplate to the stack, the method comprises the following steps:
 j) a microplate resting on the transport device is placed under the lowest microplate in the stack,
 k) the frictional connection between the lowest microplate and the lower retaining tool is released such that the lowest microplate rests on the microplate on the transport device,
 l) the transport device is moved upward until the previously lowest microplate is in contact with the second-lowest microplate above it,
 m) the frictional connection between the previously second-lowest microplate and the upper retaining tool is released such that the previously second-lowest microplate rests on the lowest microplate,
 n) the transport device is moved upward until the previously lowest microplate in the stack is at the height of the upper retaining tool,
 o) the previously lowest microplate is held by the upper retaining tool in a form-fitting manner,
 p) the transport device is moved downward until the microplate resting on the transport device is at the height of the lower retaining tool, and
 q) the microplate resting on the transport device can then be held by the lower retaining tool in a frictional manner.

The use of a frictional connection allows the transport device to directly access the microplate held with the frictional connection. This means that the transport device can be moved up to the lower surface of the microplate that is to be received thereon, and can come in direct contact therewith. In the method described above, the lower retaining tool, which is used to generate the frictional connection with the microplate, only holds one microplate at a time. It can therefore be sized accordingly.

With microplates that comprise both a container and a lid, the method is adapted accordingly, such that when removing a microplate from the stack,
 the lid on the second-lowest microplate is held by the upper retaining tool in steps e) and f), and
 the container in the second-lowest microplate is held by the lower retaining tool in steps g) and h),
and when adding a microplate to the stack,
 the microplate resting on the transport device comprises a container and a lid,
 the lid on the microplate resting on the transport device is held by the upper retaining tool in steps o) and p), and
 the container in the microplate resting on the transport device is held by the lower retaining tool in step r).

With a microplate that comprises a container and a lid, the microplate is divided in the stack between the retainer and the lid using the second retaining tool. Although the first retaining tool can fix both the container and the lid in place with a frictional connection, normally only the lid on the lowest microplate is fixed in place in the stack. The second retaining tool is then used to hold the container in the lowest microplate. This results in specific assignments for the retaining tools with regard to the two components of the microplate.

BRIEF DESCRIPTION OF THE DRAWINGS

Further advantages and features of the invention can be derived from the following description of exemplary embodiments of the invention in reference to schematic illustrations thereof. In the drawing, not to scale.

DETAILED DESCRIPTION OF THE PREFERRED EMBODIMENTS

Figure 1:
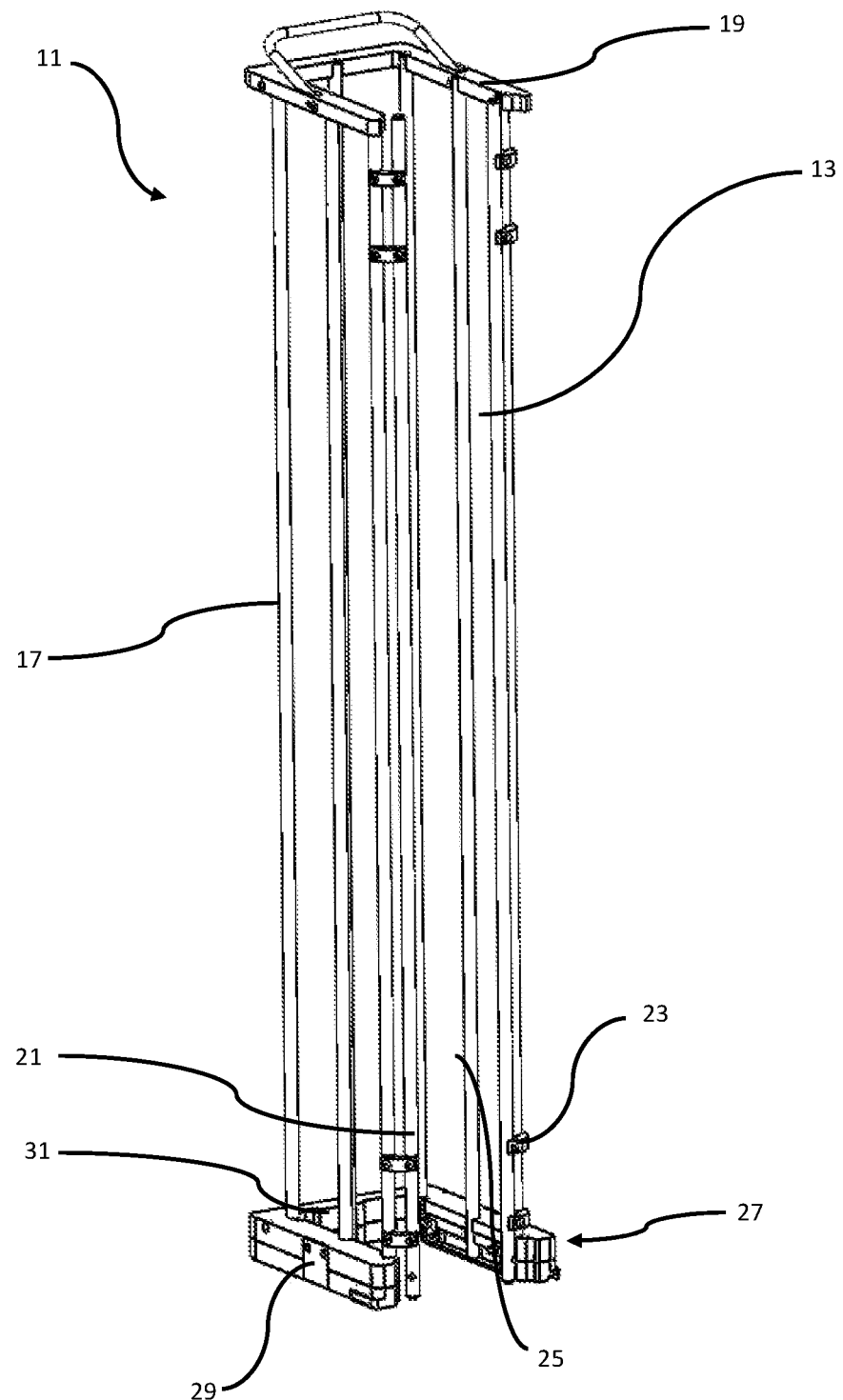
FIG. 1 shows a three dimensional view of a tower for stacked microplates.

Identical reference numerals relate to the same or functionally identical elements (in the different figures) in the following. An additional apostrophe indicates numerous instances of the same element in a drawing, and is used as needed to distinguish identical elements.

FIG. 1 shows an empty tower 13 for stacking microplates 15 (not shown). The tower 13 basically forms a rectangular structure, with the longer surfaces forming the lateral walls. The lateral walls are formed by numerous longitudinal, parallel rods 17. The cross section of the tower 13 is basically the same size as the surface area of a microplate 15, such that microplates 15 can be stacked in the tower 13, and their lateral movement is restricted by the rods 17. All but two of the rods 17 are held together at the top by a U-shaped component 19. Three of the four upper edges of the tower are covered by the U-shaped component 19. The upper ends of the two moving rods 21 are at the fourth, exposed edge, not attached to the U-shaped component 19. The side of the tower 13 where the two moving rods 21 are located forms the front side 25 of the tower. Connecting elements 23 are attached to the moving rods, which connect these rods 21 to their adjacent rods. The connecting elements 23 allow the moving rods 21 to be rotated outward about their adjacent rods. When the two moving rods 21 are rotated outward, the front 25 of the tower is open, such that microplates can be inserted laterally into the tower.

Figure 2:
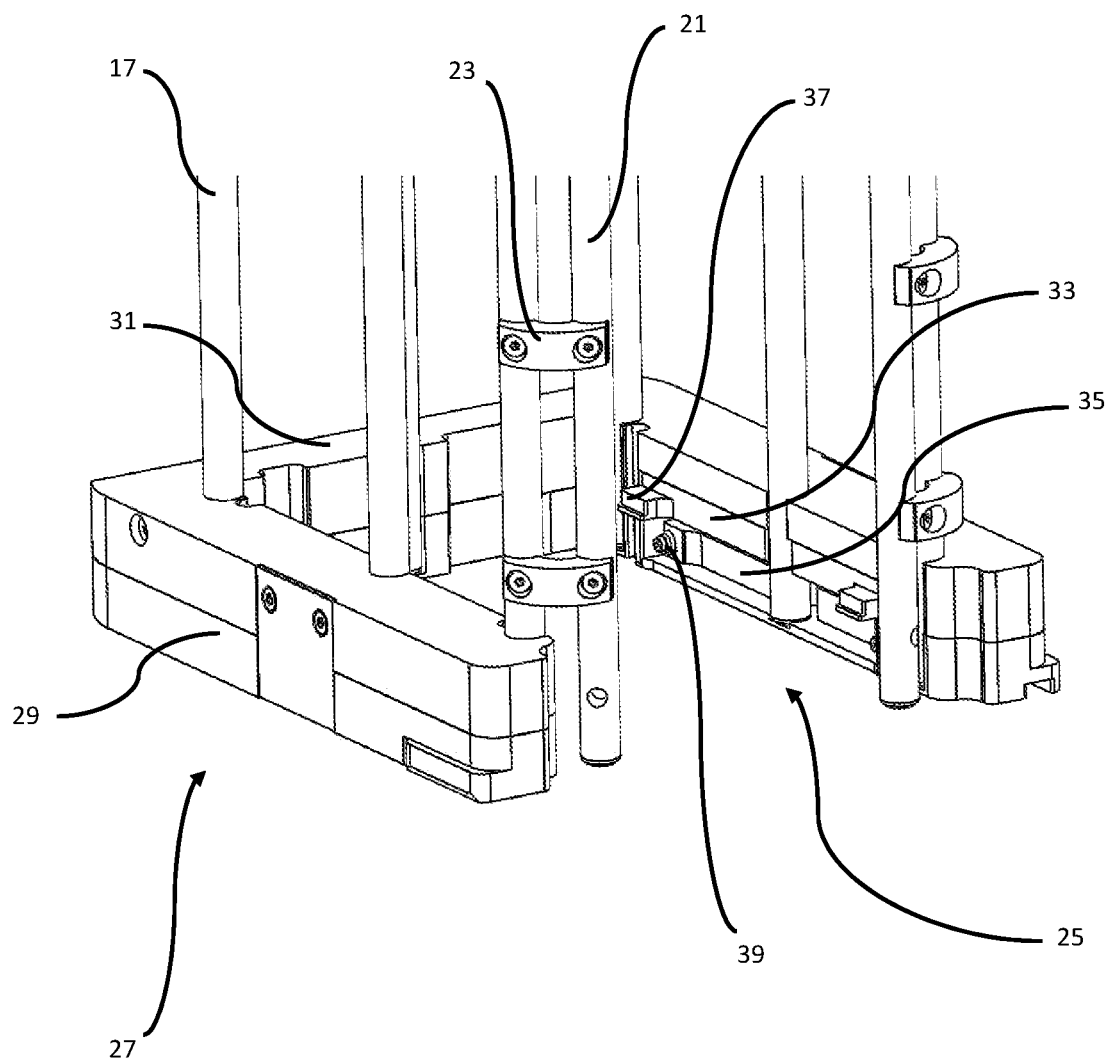
FIG. 2 shows a three dimensional view of a lower end of a tower for stacked microplates, with a retaining device thereon.

The lower end of the tower 13 and the retaining device 27 attached thereto is shown in FIG. 2. The retaining device 27 covers three of the four lower edges of the tower 13. The lower edge of the front surface 25 is exposed, like the upper edge, and is not covered. The lower ends of the two moving rods 21 are thus exposed. Because of the connecting elements 23 between the moving rods 21 and their adjacent stationary rods 17, the rods 21 can rotate about the axis of the rod it is attached to via the connecting elements 23.

The retaining device 27 has a U-shaped structure, in which two opposing sides 29, 29' are connected via a middle piece 31. The region between the two sides 29, 29' of the retaining device is empty. The empty area between the two sides 29, 29' is sized such that a transport device 30 (not shown in FIGS. 1 and 2) intended for transporting microplates can be guided through this area in the tower 13. Two retaining tools 33, 35 are arranged vertically in the side 29 of the retaining device 27. The upper retaining tool 33 comprises two grippers 37. The grippers 37 face the interior of the tower 13. The two grippers 37 are at the same height, but on different ends of the upper retaining tool 33. The upper retaining tool 33 can move toward the interior of the tower 13 and back away therefrom. There is a recess in the middle of the inner surface of the upper retaining tool 33, through which a rod 17 passes. The recess is formed such that the retaining tool 33 can move back and forth toward the interior of the tower 13. The lower retaining tool 35 is located below the upper retaining tool 33. The lower retaining tool 35 has to bolts 39 facing the interior of the tower 13. There is a recess in the middle of the inner surface of the lower retaining tool 35, through which the same rod passes that passes through the recess in the upper retaining tool 33.

Figure 3:
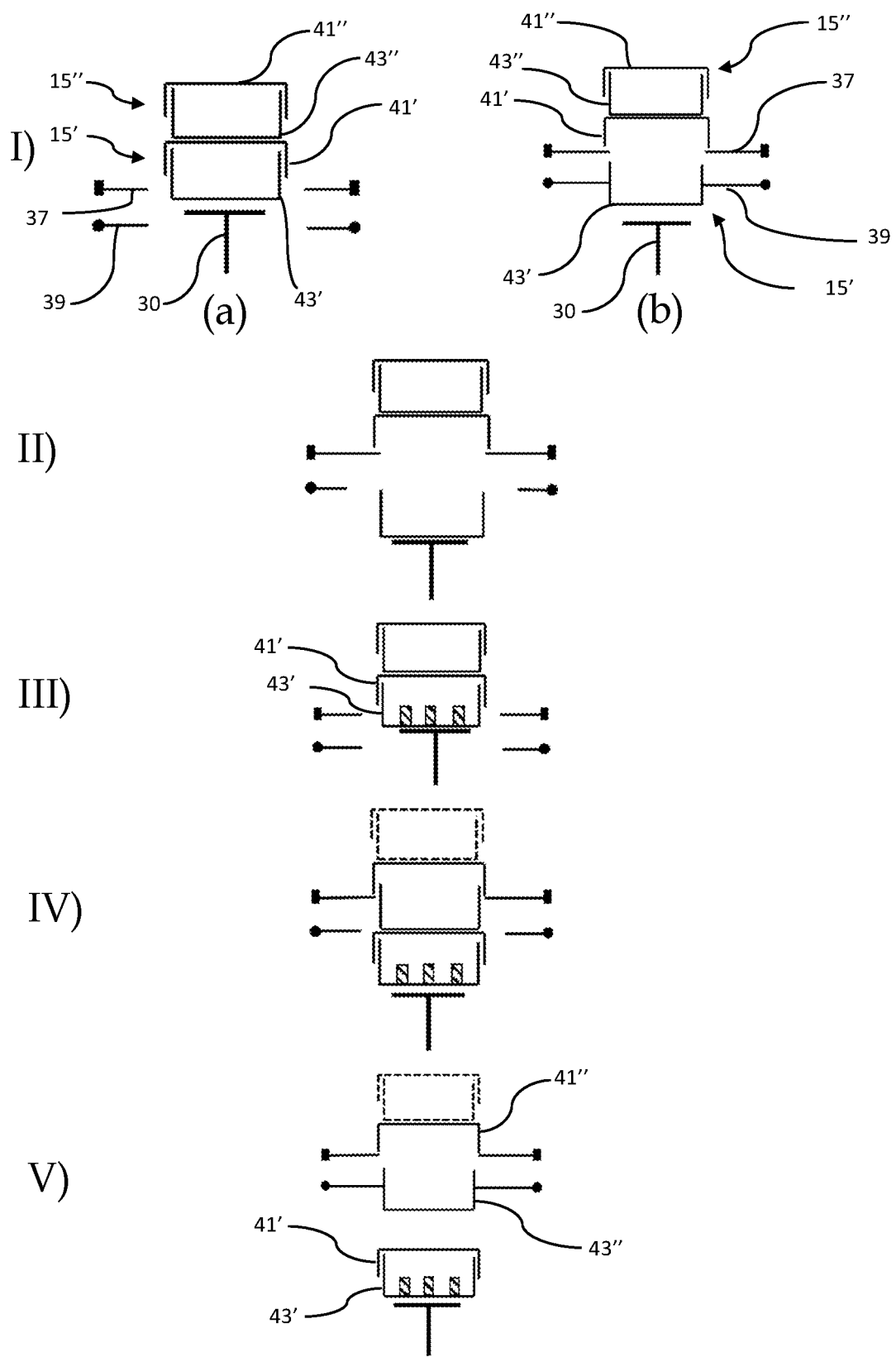
FIG. 3 shows a method sequence in steps I)-V) for removing microplates from a device according to the invention.

The functioning of the device according to the invention is shown in individual process steps in FIG. 3. The lowest microplate 15' in the stack of microplates 15 in the tower is transported in this process. The microplates 15 are transported with a transport device 30 that is able to access the lowest microplate 15' in a stack. This device is therefore able to transport the lowest microplate 15' in a stack. At the start, the lowest microplate 15' is fixed in place by the retaining device 27. The lowest microplate 15 can rest with its lid 41' and container 43' on the grippers 37 in the upper retaining tool 33 in a first possible starting position (a). In a second possible starting position (b), the lid 41' on the lowest microplate 15' rests on the grippers 37, and the container 43' in the lowest microplate 15' is fixed in place by the bolts 39 in the lower retaining tool 35. The grippers 37 in the upper retaining tool 33 hold the microplate 15 in a form-fitting connection, while a frictional connection is established with the bolts 39 in the lower retaining tool 35, which fixes the microplate 15 in place. The starting position is shown in the first process step I).

Starting from the first starting position (a), the transport device 30 is placed under the lowest microplate 15' such that the transport device 30 can support the entire weight of the microplate stack. The form-fitting connection obtained with the grippers 37 is then released, such that the lowest microplate 15' can be moved downward with the transport device 30. The grippers 37 are then moved inward as soon as the lower edge of the container 43' of the lowest microplate 15' lies below the grippers 37. The lid 41' of the lowest microplate 15' is then resting on the grippers 37, while the container 43' of the lowest microplate 15' rests on the transport device 30, and can be removed for further treatment, as is shown in process step II).

In the second starting position (b), the lid 41' on the lowest microplate 15' is already on the grippers 37, and the container 43' in the lowest microplate 15' is fixed in place by the bolts 39 through a frictional connection. The transport device 30 is again moved underneath the container 43' in the lowest microplate 15'. At this point, the frictional connection can be released by retracting the bolts 39. The container 43' in the lowest microplate then rests on the transport device 30, as shown in process step II).

After the container 43' in the lowest microplate 15' has been processed, it is returned to the stack with the transport device 30. The container 43' is placed below the lid 41' on the lowest microplate 15' such that the lid 41' is flush with the container 43'. The grippers 37 are then retracted, thus releasing the frictional connection to the lid 41 on the lowest microplate 15', such that the entire weight of the stack rests on the transport device 30. This is shown in process step III).

When the processing of the lowest microplate 15' is completed, it is then transported away with both the container 43' and the lid 41'. The transport device 30 now located beneath the container 43' in the lowest microplate 15' moves downward until the grippers 37 are then located between the lower edge of the container 43" and the lower edge of the lid 41" of the second-lowest microplate 15". By moving the grippers 37 inward, and the transport device 30 further downward, the lid 41" of the second-lowest microplate 15" then rests on the grippers 37. The lowest microplate 15' and the container 43" in the second-lowest microplate 15" therefore remain on the transport device 30, as shown in process step IV).

The container 43" in the second-lowest microplate 15" is fixed in place by the by the bolts 39 in the second retaining tool 35. The bolts 39 are moved inward for this when the container 43" is at their height, as is shown in process step V). When the transport device 30 is moved, only the lowest microplate 15' remains on the transport device 30. It has already been processed here, and can then be removed in accordance with its application. The second-lowest microplate 15" is then at the position of the lowest microplate 15' in the second starting situation (b) shown in process step I).

Two of the devices 11 according to the invention can be used in a system, with just one transport device 30. By way of example, empty microplates 15 can be removed from a first tower 13, and then placed in the second tower 13 with the same transport device after they have been filled.

Figure 4:
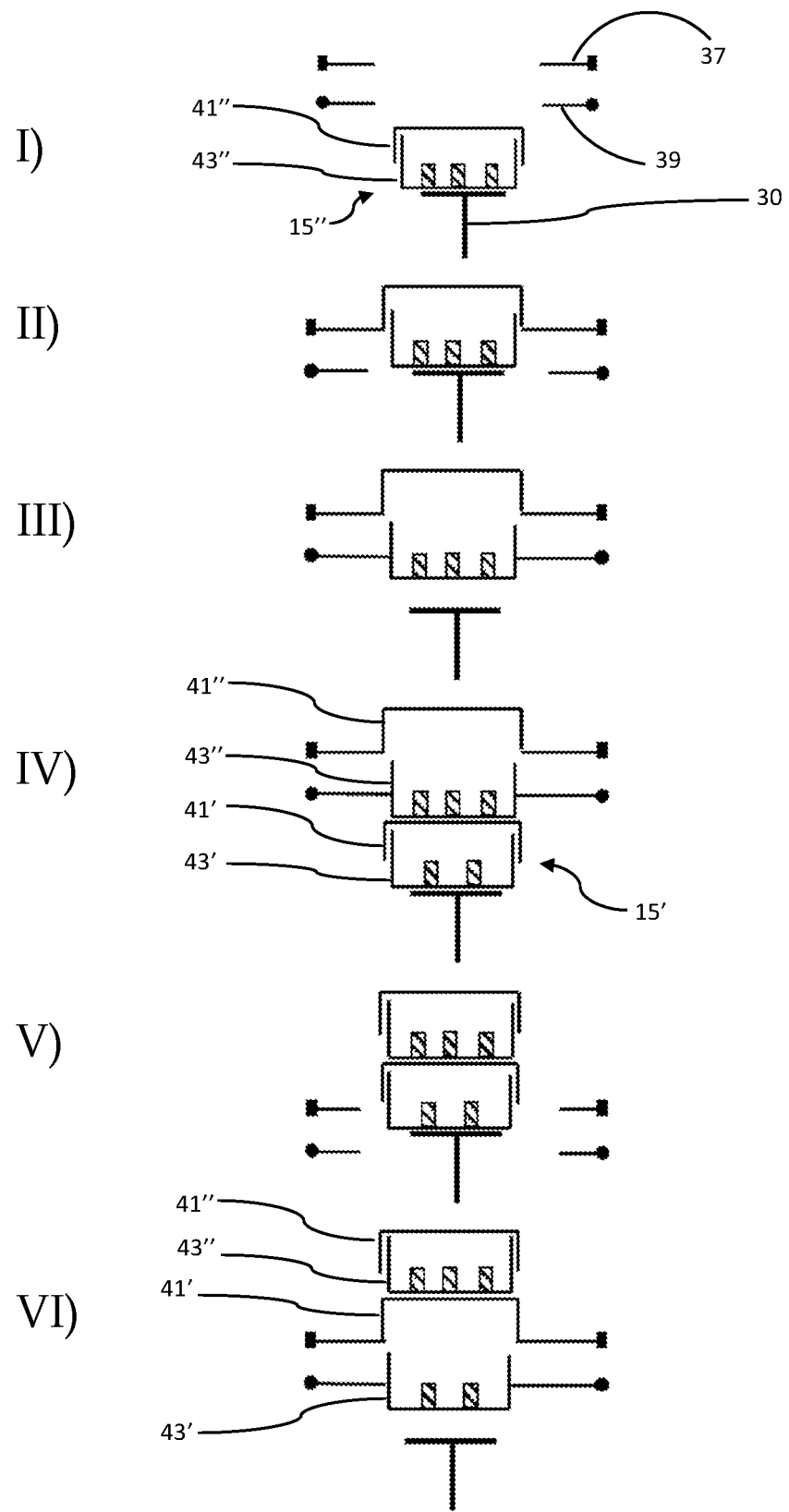
FIG. 4 shows a method sequence in steps I)-VI) for receiving and stacking microplates in a device according to the invention.

A process for stacking microplates 15 in a device 11 according to the invention is shown schematically in FIG. 4. The process is divided into six steps, which shall be described in detail below.

The tower 13 is empty in the first process step I), and a filled microplate 15" is placed on the transport device 30. The transport device 30 is moved upward with the microplate 15", and thus into the tower 13, until the lower edge of the lid 41" on the microplate is above the grippers 37 in the upper retaining tool 33. The grippers 37 are then extended. When the transport device 30 moves downward, the lid 41" on the microplate remains on the grippers 37. The lid 41" on the microplate is fixed in place by the form-fitting connection, as shown in process step II). When the transport device 30 has moved further downward, such that the container 43" in the microplate is at the height of the lower retaining tool 35, the bolts 39 in the lower retaining tool 35 are extended. The bolts 39 fix the container 43" in the microplate 15" in place with the frictional connection. There are therefore no microplates resting on the transport device, and the transport device 30 is then ready to receive another microplate 15. This is shown in process step III). A new filled microplate 15' now lies on the transport device 30 and is ready to be stacked. The bolts 39 allow for access to the entire lower surface of the microplate due to the lateral frictional effect acting on the container 43" therein. The transport device 30 can then be moved upward with the microplate 15' until the upper surface of the lid 41' on the lower microplate 15' comes in contact with the lower surface of the container 43" in the upper microplate 15". The bolts 39 can be retracted, releasing the frictional connection, without altering the position of the container 43" in the upper microplate 15". This is shown in process step IV). When the transport device 30 then moves upward, the container 43" in the upper microplate 15" comes in contact with the lid 43" that is lying on the grippers 37. After this contact takes place, the grippers 37 are retracted. The retraction of the grippers 37 does not result in any movement of a microplate. The transport device 30 is moved further upward, until the lower edge of the lid 41' on the lower microplate 15' is above the bolts 39, as shown in process step V). The transport device 30 is then moved back downward, and the processes in steps II) and III) described above are repeated, in order to fix the lid 41' on the container 43' in the lower microplate 15' in place. The lid 41' on the lower microplate 15' then rests on the grippers 37 while the container 43' in the lower microplate 15' is fixed in place by the bolts 39 with a frictional connection thereto. This is shown in process step VI), and is congruent to the state shown in process step III). The procedures in process steps III) and VI) can then be repeated as often as necessary to continue stacking microplates 15.

A device according to the invention can also stack microplates that have containers without lids. If the grippers 37 fix the lowest microplate 15' in place, the second-lowest microplate 15" then rests on the bolts 39.

Figure 5:
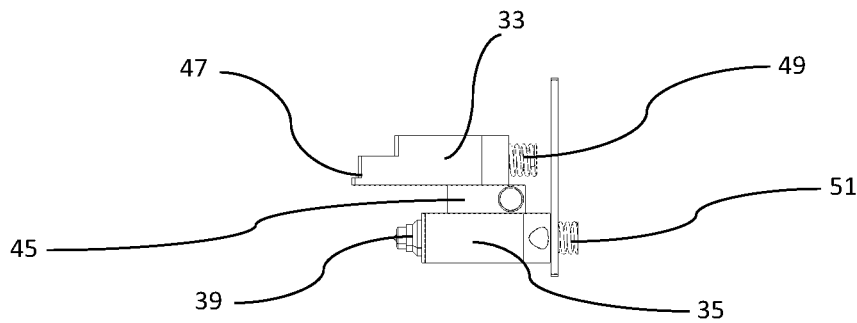
FIG. 5 shows a cross section of a retaining device that has grippers and bolts in a vertical arrangement.

A cross section of a side 29 of the retaining device is shown in FIG. 5, in which the upper and lower retaining tools 33, 35 can be seen in their entirety. A slide bar 45 is placed between the two retaining tools 33, 35. The upper and lower retaining tools 33, 35 are each attached to the retaining device 27 via a spring 49, 51, respectively. The movement of the slide bar 45 triggers the movements of the two retaining tools 33, 35. The slide bar 45 is connected to the two retaining tools 33, 35 such that that the movement of the upper retaining tool 33 is triggered first. The movement of the lower retaining tool 35 can only be triggered when the upper retaining tool 33 has already moved into its extended position. The springs 49, 51 on the retaining tools 33, 35 are under tension when the retaining tools 33, 35 are not extended and still in their starting positions.

Figure 6:
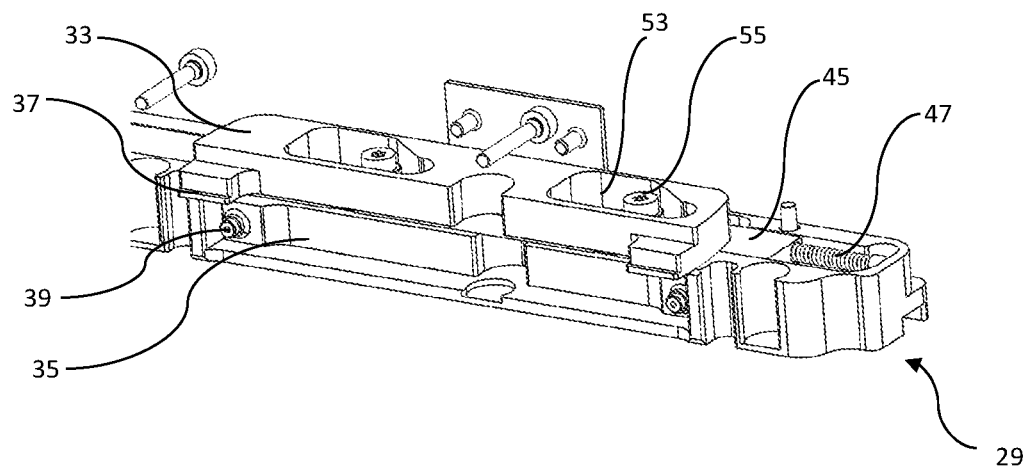
FIG. 6 shows a three dimensional view of a retaining device according to a first embodiment, with a slide bar.
Figure 7:
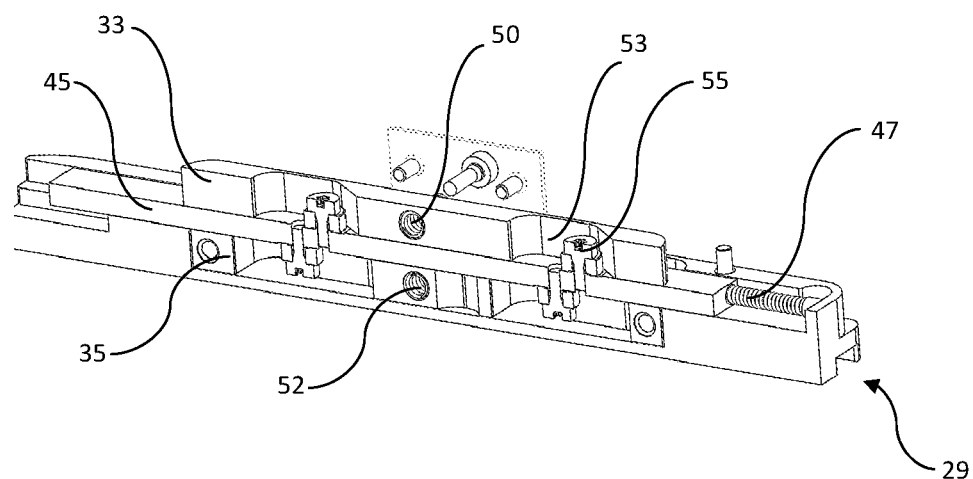
FIG. 7 shows a cross section of the retaining device shown in FIG. 6.

One side of the retaining device 29 is shown with the two retaining tools 33, 35 and the slide bar 45 in FIGS. 6 and 7. The upper retaining tool 33 has two grippers 37 on its front end. These are located on the ends of the longitudinal side of the upper retaining tool 33, such that the grippers 37 are at a maximum distance to one another. There are two holes 53 in the upper retaining tool 33, which pass from the upper surface to the lower surface of the retaining tool 33. A sliding block 55 is placed in each of these holes, which is then attached to the slide bar 45, as shown in FIG. 7. The holes 53 each form a connecting passage, such that by moving the slide bar 45, the relative position of the sliding block 55 is altered laterally to the slide bar in relation to the retaining tool 33. The change in the relative position of the sliding block 55 with respect to the upper retaining tool 33 allows the upper retaining tool to be moved laterally in relation to the slide bar. This movement is forced by the spring 49 (not shown), which is under tension when the retaining tool has not been extended.

The slide bar 45 is attached to the retaining device 27 by a spring plunger 47. The spring on the spring plunger 47 is a compression spring, such that the spring on the spring plunger 47 is under tension when the retaining tools 33, 35 are retracted.

The sliding blocks 55 for the upper retaining tool 33 are attached to the upper surface of the slide bar 45. Sliding blocks 55 for the lower retaining tool 35 are attached to the lower surface of the slide bar 45. These are offset to those on the upper surface in the longitudinal direction of the slide bar 45. The lower retaining tool 35 also has two holes 53, which pass from the upper surface to the lower surface thereof. These holes 53 have basically the same shape as those in the upper retaining tool 33, but the holes 53 in the lower retaining tool 35 are offset to those in the upper retaining tool 33 in the longitudinal direction of the slide bar 45.

Because the holes 53 in the upper and lower retaining tools 33, 35, are offset, and the sliding blocks are offset to one another on the upper and lower surfaces of the slide bar 45, the sliding blocks 55 in the lower retaining tool 35 and those in the upper retaining tool 33 move sequentially when the slide bar 45 is moved. In the retaining device 27 shown in FIG. 6, the upper retaining tool 33 must have been already moved before the lower retaining tool 35 can move. Depending on the position of the slide bar 45, it is possible to move only the upper retaining tool 33 back and forth.

FIG. 7 shows the holes 50, 52 for the springs 49, 51 with which the retaining tools 33, 35 are attached to the retaining device 27. The holes 50, 52 are each formed in basically the middle of the retaining tools 33, 35 in order to eliminate the formation of any torque when the springs 49, 51 extend, and to ensure that the two grippers 37 and two bolts 39 in the respective retaining tools 33, 35 always move simultaneously.

Figure 8:
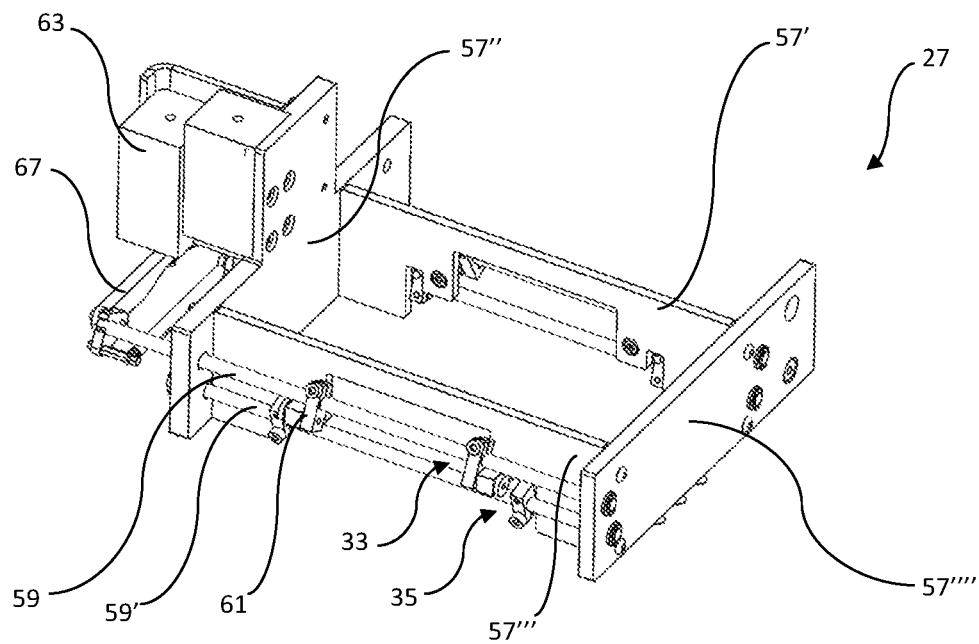
FIG. 8 shows a three dimensional view of a retaining device according to a second embodiment, with a rocker arm assembly.
Figure 9:
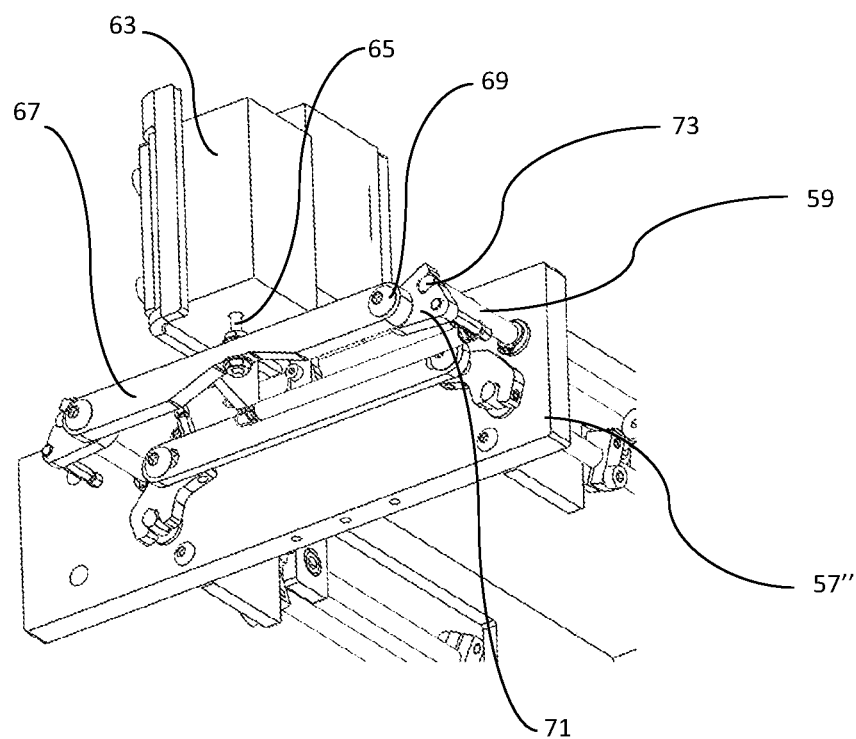
FIG. 9 shows a detailed view of the rocker arm assembly in the retaining device shown in FIG. 8.

An alternative retaining device 27 is shown in FIGS. 8 and 9. The retaining device 27 has four walls, encompassing all four sides of the lower end of the tower (not shown). Retaining tools 33, 35 are attached to two opposing walls 57', 57''' of the retaining device 27. These walls have holes that allow the retaining tools 33, 35 to pass through the walls from the outside to the inside of the retaining device 27. The walls 57', 57''' are attached with screws to the other two walls 57'', 57'''' of the retaining device, such that the walls 57', 57''' extend from one wall 57'' to the other wall 57''''. The walls 57'', 57'''' extend beyond the edges of the walls 57', 57''' and each have two holes there. These holes are placed such that two cylindrical rods 59, 59' can pass through the four holes, such that the cylindrical rods 59, 59' are located above one another, and can be rotated in the holes. The retaining tools 33, 35 are attached to the cylindrical rods 59, 59', and each retaining tool has two retaining bodies 61 permanently attached thereto, and each retaining body 61 has a pin attached to it. The pins form those parts of the retaining tools 33, 35 that can be inserted into the retaining device.

The drive that moves the cylindrical rod 59, and therefore the retaining tools 33, 35, is attached to a wall 57'' that is perpendicular to the two walls 57', 57'''. The drive comprises two actuators 63, with which the rotation of the cylindrical rods 59, 59' is obtained via a rocker arm assembly. The first actuator 63 is placed in the middle of the wall 57'', and the second actuator is placed on the other side of the wall 57'', opposite the first actuator. Both actuators have a plunger 65, which can move downward in the stacking direction of the device 11. The plungers 65 form the connections between the actuators 63 and a respective transfer rod 67 that is perpendicular to the plungers, which has a hole at each end. Bolts 69 pass through the holes in the transfer rods 67, which connect the transfer rods 67 at their ends to a respective rocker arm 71. The plungers 65 are attached to the middles of the transfer rods 67, such that the movements of the plungers 65 do not result in a torque being applied to the transfer rods 67. The rocker arms 71 each have a cut-out 73 in the form of an open-ended wrench, in addition to a hole 75 for receiving the bolt. These cut-outs receive the cylindrical rods 59. The cylindrical rods 59 have a polygonal cross section at their ends where they are connected to the actuators 63. The polygonal cross sections enable a torque obtained when the rocker arms 71 are rotated to be applied to the cylindrical rods. The cut-out 73 in the form of an open-ended wrench is permanently connected to the cylindrical rod 59, such that when the bolt 69 is moved in the hole 75, the rocker arm 71 only rotates about the cylindrical rod 59, thus rotating the cylindrical rod 59.

Although specific embodiments have been described above, it is clear that different combinations of the possible embodiments can be made use of, as long as the various possible embodiments are not mutually exclusive.

The invention claimed is:

1. A device (11) configured for receiving, stacking, and removing microtiter plates (15) comprising a container (43) or a container (43) with a lid (41), the device comprising:
   a tower (13) for stacking a plurality of microtiter plates (15) on top of each other in a stack, the tower having a cross section suitable to hold the microtiter plates and restrict lateral movement of the stack of microtiter plates,
   a retaining device (27) at the lower end of the tower, which has an upper retaining tool (33) and a lower retaining tool (35), wherein the upper retaining tool (33) is located above the lower retaining tool (35) and configured to selectively hold a microtiter plate (15) in a form-fitting manner to prevent downward movement of the microtiter plate and support the weight of all the microtiter plates stacked on the microtiter plate, and the lower retaining tool (35) is configured to fix the lowest microtiter plate in place in the lower retaining tool (35) by frictionally engaging sidewalls of the lowest microtiter plate; and
   a slide bar (45) attached to the retaining device (27) which triggers the movements of the two retaining tools (33, 35), wherein the slide bar (45) is placed on the retaining device (27) and is connected to the two retaining tools (33, 35) such that the slide bar (45) triggers the movement of the upper retaining tool (33) in a first step, and triggers the movement of the lower retaining tool (35) in a second step.

2. The device (11) according to claim 1, wherein there is a movable gripper (37) on the upper retaining tool (33) configured to move inward towards the middle of the tower and having an horizontal extension that extends inward and is configured to support vertical weight placed on the horizontal extension.

3. The device (11) according to claim 1, wherein the retaining device (27) has two upper and lower retaining tools (33, 35), which are placed opposite one another and can be moved towards one another and towards the middle of the tower for interacting with adjacent microtiter plates of the stack of microtiter plates.

4. The device according to any of the claim 2, wherein two bolts (39) are attached to the lower retaining tool (35), and the bolts (39) is configured to frictionally engage and fix the container (43) of the lowest microtiter plate in the stack in place in the lower retaining tool.

5. The device (11) according to claim 2 wherein the upper retaining tool (33) has two movable grippers (37).

6. The device (11) according to claim 1, wherein the upper retaining tool (33) is connected to the retaining device (27) via a first spring element (49) comprising a compression spring.

7. The device (11) according to claim 1, wherein the lower retaining tool (35) is connected to the retaining device (27) via a second spring element (51) comprising a compression spring.

8. The device (11) according to claim 1, wherein the upper and lower retaining tools (33, 35) are mounted on the retaining device (27) such that they can move toward the middle of the tower (13).

9. A system that contains a device (11) for receiving, stacking, and removing microplates (13) according to claim 1, a dispenser device for filling microplates, and a transport device (30) for adding and removing microplates to and from the device (11).

10. The system according to claim 9, comprising a first and second device (11) for receiving, stacking, and removing microplates, wherein the two devices share a single transport device (30).

11. The device (11) according to claim 1, wherein:
   the upper retaining tool (33) is configured to hold the lid of the lowest microtiter plate (15) by extending grippers underneath the sidewalls of the lid such that at least a portion of the grippers positively hold the weight of the stack from underneath the sidewalls of the lid;

and the lower retaining tool (35) is configured to hold the container of the lowest microtiter plate by frictional engagement of at least two opposing sidewalls of the lowest microtiter plate.

12. The device (11) according to claim 1, wherein:

the lower retaining tool (35) is configured to hold the container of the lowest microtiter plate by frictional engagement of at least two opposing sidewalls of the lowest microtiter plate;

the upper retaining tool (33) is configured to hold an adjacent microtiter plate above and adjacent the lowest microtiter plate in the stack by extending grippers underneath sidewalls of the adjacent microtiter plate such that at least a portion of the grippers positively hold the weight of the stack from underneath the adjacent microtiter plate thereby enabling the lowest microtiter plate to be removed from in the stack when the frictional engagement of the lower retaining tool is released.

13. The device (11) according to claim 2, wherein the gripper (37) when extended reaches almost to the lateral wall of the container (43) of a microtiter plate (11) received in the tower (13).

14. The device (11) according to claim 1, wherein the tower comprises several stationary longitudinal parallel rods and one or two movable longitudinal parallel rods, said movable longitudinal parallel rods being able to rotate outward to open the tower and enable a stack of microtiter plates to be loaded into the tower or removed from the tower.

\* \* \* \* \*